(12) United States Patent
Okuda et al.

(10) Patent No.: US 9,138,158 B2
(45) Date of Patent: Sep. 22, 2015

(54) BIOLOGICAL INFORMATION DETECTING APPARATUS AND FIXING STRUCTURE

(71) Applicant: SEIKO INSTRUMENTS INC., Chiba (JP)

(72) Inventors: Hideki Okuda, Chiba (JP); Teruo Kato, Chiba (JP); Dai Terasawa, Chiba (JP)

(73) Assignee: SEIKO INSTRUMENTS INC. (JP)

( * ) Notice: Subject to any disclaimer, the term of this patent is extended or adjusted under 35 U.S.C. 154(b) by 65 days.

(21) Appl. No.: 14/041,003

(22) Filed: Sep. 30, 2013

(65) Prior Publication Data
US 2014/0094677 A1 Apr. 3, 2014

(30) Foreign Application Priority Data

Oct. 2, 2012 (JP) .................. 2012-220392

(51) Int. Cl.
*A61B 5/0408* (2006.01)
*A61B 5/00* (2006.01)
*A61B 5/024* (2006.01)
*A61B 5/0245* (2006.01)

(52) U.S. Cl.
CPC .......... *A61B 5/0408* (2013.01); *A61B 5/02438* (2013.01); *A61B 5/04085* (2013.01); *A61B 5/6823* (2013.01); *A61B 5/6831* (2013.01); *A61B 5/0245* (2013.01)

(58) Field of Classification Search
CPC ... A61B 5/0485; A61B 5/6823; A61B 5/6831
USPC .................. 600/390, 393; 607/149
See application file for complete search history.

(56) References Cited

U.S. PATENT DOCUMENTS

| 5,464,021 | A | * | 11/1995 | Birnbaum | 600/509 |
| 5,778,880 | A | * | 7/1998 | Chen | 600/509 |
| 6,272,365 | B1 | * | 8/2001 | Ronkainen et al. | 600/390 |
| 7,167,737 | B2 | * | 1/2007 | Fujii et al. | 600/390 |
| 7,330,751 | B2 | | 2/2008 | Ueda | 600/509 |
| 2009/0131759 | A1 | * | 5/2009 | Sims et al. | 600/301 |

* cited by examiner

*Primary Examiner* — Lee S Cohen
(74) *Attorney, Agent, or Firm* — Adams & Wilks (57) ABSTRACT

A biological information detecting apparatus has an apparatus main body, a pair of biological signal detecting parts provided on the apparatus main body, a fixing part attached to the apparatus main body, holders provided to be slidable along a longitudinal direction of the fixing part, and joining parts configured to releasably join the pair of biological signal detecting parts to the respective holders. Each of the biological signal detecting parts has an electrode adapted to be in contact with a biological surface of a user's body. The fixing part is configured to fix the apparatus main body and the pair of biological signal detecting parts to the user's body.

20 Claims, 7 Drawing Sheets

BIOLOGICAL INFORMATION DETECTING APPARATUS AND FIXING STRUCTURE

BACKGROUND

1. Technical Field

The present invention relates to a biological information detecting apparatus that detects biological signals by attaching electrodes to a biological surface of a body and, and to a fixing structure enabling the detection of the biological signals by the biological information detecting apparatus.

2. Related Art

Some biological information detecting apparatuses of this type detect cardiac signals generated in connection with heartbeats and measure heart rate from a biological surface, for example. There is a biological information detecting apparatus of this type including a pair of electrodes and an apparatus main body (transmission unit), for example. The apparatus main body is electrically connected to the respective electrodes through wires. Each of the electrodes has a hook for holding the electrode at a predetermined portion of a body by clipping a lower portion of clothes or the like attached to the body. Thus, clothes or the like press the pair of electrodes against the biological surface.

There is also a biological information detecting apparatus in which an attachment belt for holding the electrodes at predetermined portions of a body is separately provided instead of clothes or the like. In this attachment belt, a cut for receiving the hook is formed so that the positions of the electrodes with respect to the attachment belt are not deviated.

With this configuration, the pair of electrodes detects cardiac signals generated in connection with heartbeats, whereby heart rate is measured (for example, refer to Japanese Patent No. 4439856).

However, in the related art described above, when the electrodes are held by the hook clipping clothes or the like, it is difficult to generate a holding force sufficient for the electrodes only by a clipping force of the hook. Therefore, depending on a way of movement of a wearer, the electrodes are deviated from or fall off clothes or the like, and thus the pressing force for pressing the electrodes against the biological surface may be lowered or lost, which leads to a problem in that the heart rate cannot be detected favorably.

Meanwhile, when the electrodes are held by inserting the hook through the cut of the attachment belt, the positions of the electrodes with respect to the attachment belt are not deviated, so that the pressing force for pressing the electrodes against the biological surface is not lowered or lost. However, when the attachment belt expands or contracts following the movement of the wearer, the positions of the electrodes are deviated following the expansion or contraction of the attachment belt. Therefore, the contact positions of the electrodes with respect to the biological surface are unstable, which leads to a problem in that the heart rate cannot be detect favorably.

The present invention has been made in view of the aforementioned situation and an object thereof is to provide a biological information detecting apparatus that can detect biological signals stably and favorably, and to a fixing structure that enables such detection.

SUMMARY

In order to solve the problems described above, a biological information detecting apparatus according to an embodiment of the present invention includes: an apparatus main body; a pair of biological signal detecting parts provided on the apparatus main body, each of the biological signal detecting parts having an electrode in contact with a biological surface; a strip-shaped fixing part attached to the apparatus main body and configured to fix the apparatus main body and the pair of biological signal detecting parts to a body; holders provided to be slidable along a longitudinal direction of the fixing part; and joining parts configured to join the pair of biological signal detecting parts and the holders.

With this configuration, the positions of the biological signal detecting parts with respect to the fixing part are not deviated, and thus, the fixing part can always apply pressing force to the electrodes against the biological surface. In addition, for example, even when the fixing part expands and contracts according to the movement of the wearer, the holders slide along the longitudinal direction of the fixing part, and thus the electrodes are not deviated following the expansion and contraction of the fixing part. Therefore, biological signals can be detected stably and favorably.

Further, since the holders concentrically press the electrodes, the pressing force applied to the electrodes increases at the positions of the holders. Therefore, accuracy of detection by the biological signal detecting parts can be improved.

In the biological information detecting apparatus according to an embodiment of the present invention, the holders may be positioned at portions corresponding to ends, which are opposite to the apparatus main body, of the electrodes.

With this configuration, a sufficient distance can be secured between the portions that are pressed by the holders of the respective electrodes. Therefore, accuracy of detection by the biological signal detecting parts can be improved.

In the biological information detecting apparatus according to an embodiment of the present invention, each of the joining parts may include a protrusion provided on the biological signal detecting part side and a recess provided on the holder side and capable of receiving the protrusion.

With this configuration, the pair of biological signal detecting parts and the holders can be joined with the simple structure.

In the biological information detecting apparatus according to an embodiment of the present invention, the protrusion may be press-fitted into the recess.

With this configuration, the pair of biological signal detecting parts and the holders can be reliably joined. In addition, biological signals can be detected stably and favorably.

In the biological information detecting apparatus according to an embodiment of the present invention, each of the holders may be formed to surround a circumference of the fixing part in a short-length direction thereof, and a slit may be formed to cut the holder in a short-length direction thereof.

With this configuration, the holder can be attached to the fixing part by inserting the fixing part through the slit. Therefore, workability upon maintenance such as cleaning of the fixing part can be improved.

In the biological information detecting apparatus according to an embodiment of the present invention, the slit may be formed to cut a portion of the holder where the recess is formed.

With this configuration, diameter expansion of the recess can be easy when the protrusion is press-fitted into the recess of the holder. Thus, a press-fit force of the protrusion with respect to the recess can be maintained constant without the need of controlling manufacturing accuracy of the recess and the protrusion with high accuracy. Therefore, when the recess and the protrusion are press-fitted, manufacturing cost can be reduced.

In the biological information detecting apparatus according to an embodiment of the present invention, each of the joining parts may include surface fasteners respectively provided on each of the biological signal detecting parts and each of the holders.

With this configuration, the position for attaching the holder with respect to the biological signal detecting part can be adjusted. Therefore, biological signals can be detected more stably and favorably.

In the biological information detecting apparatus according to an embodiment of the present invention, each of the biological signal detecting parts, each of the holders, and each of the joining parts may be formed integrally.

With this configuration, the respective parts can be controlled easily and assemblability of the biological information detecting apparatus can be improved.

A fixing structure according to an embodiment of the present invention includes: a pair of biological signal detecting parts provided on an apparatus main body, each of the biological signal detecting parts having an electrode in contact with a biological surface; a strip-shaped fixing part attached to the apparatus main body and configured to fix the apparatus main body and the pair of biological signal detecting parts to a body; holders provided to be slidable along a longitudinal direction of the fixing part; and joining parts configured to join the pair of biological signal detecting parts and the holders, wherein the fixing part, the holders, and the joining parts fix the biological signal detecting parts to the body.

With this configuration, the apparatus main body and the pair of biological signal detecting parts can be fixed reliably, and thus biological signals can be detected stably and favorably.

According to an embodiment of the present invention, the positions of the biological signal detecting parts with respect to the fixing part are not deviated, and thus, the fixing part can always apply pressing force to the electrodes against the biological surface. In addition, for example, even when the fixing part expands and contracts according to the movement of the wearer, the holders slide along the longitudinal direction of the fixing part, and thus the electrodes are not deviated following the expansion and contraction of the fixing part. Therefore, biological signals can be detected stably and favorably.

Further, since the holders concentrically press the electrodes, the pressing force applied to the electrodes increases at the positions of the holders. Therefore, accuracy of detection by the biological signal detecting part can be improved.

DETAILED DESCRIPTION

First Embodiment

Heart Rate Measuring Apparatus

Next, a first embodiment of the present invention will be described with reference to FIGS. 1 to 4.

Figure 1:
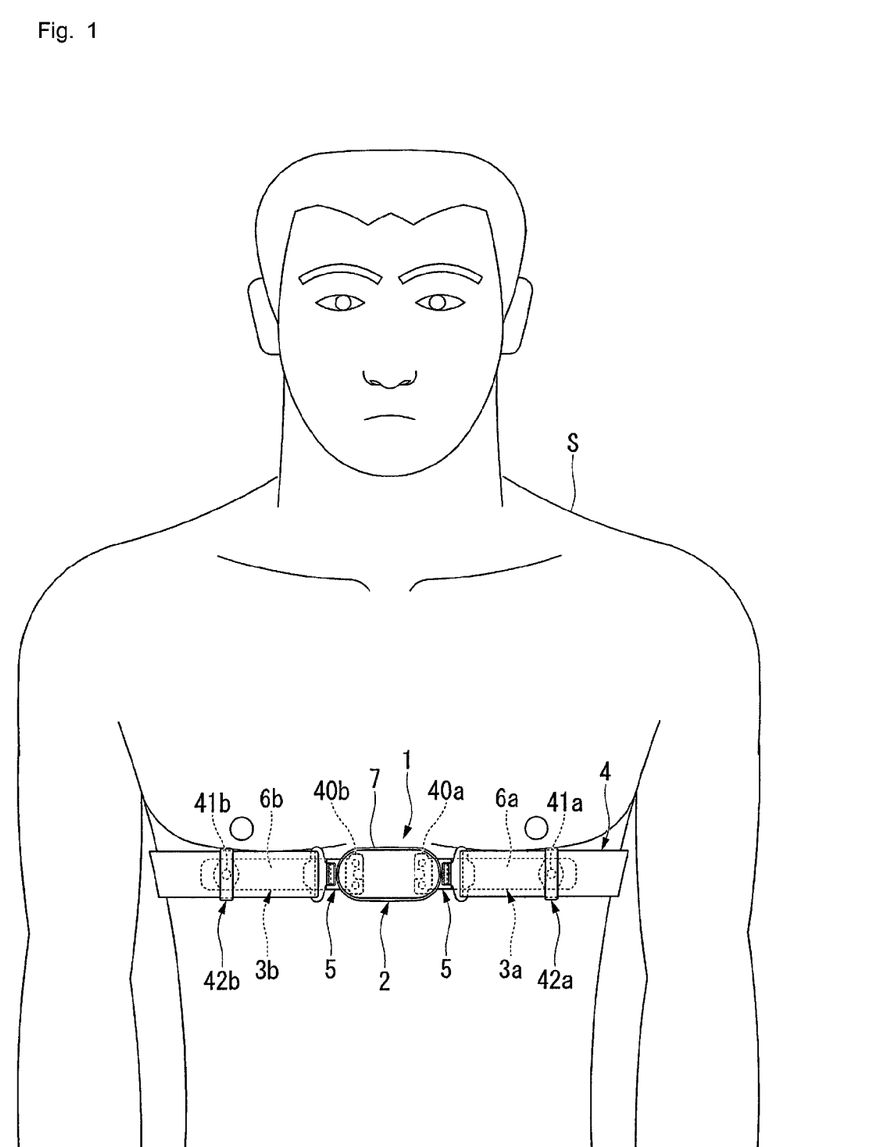
FIG. 1 is a front view of a heart rate measuring apparatus according to a first embodiment of the present invention attached to a wearer.
Figure 2:
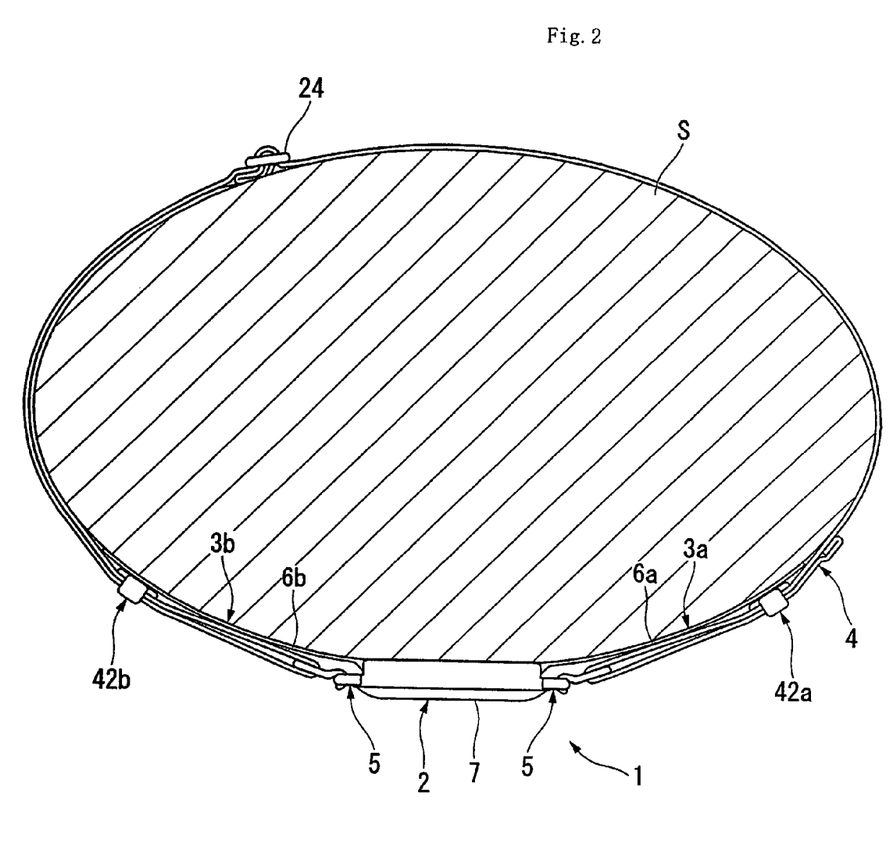
FIG. 2 is a side sectional view of the heart rate measuring apparatus according to the first embodiment of the present invention attached to the wearer.
Figure 3:
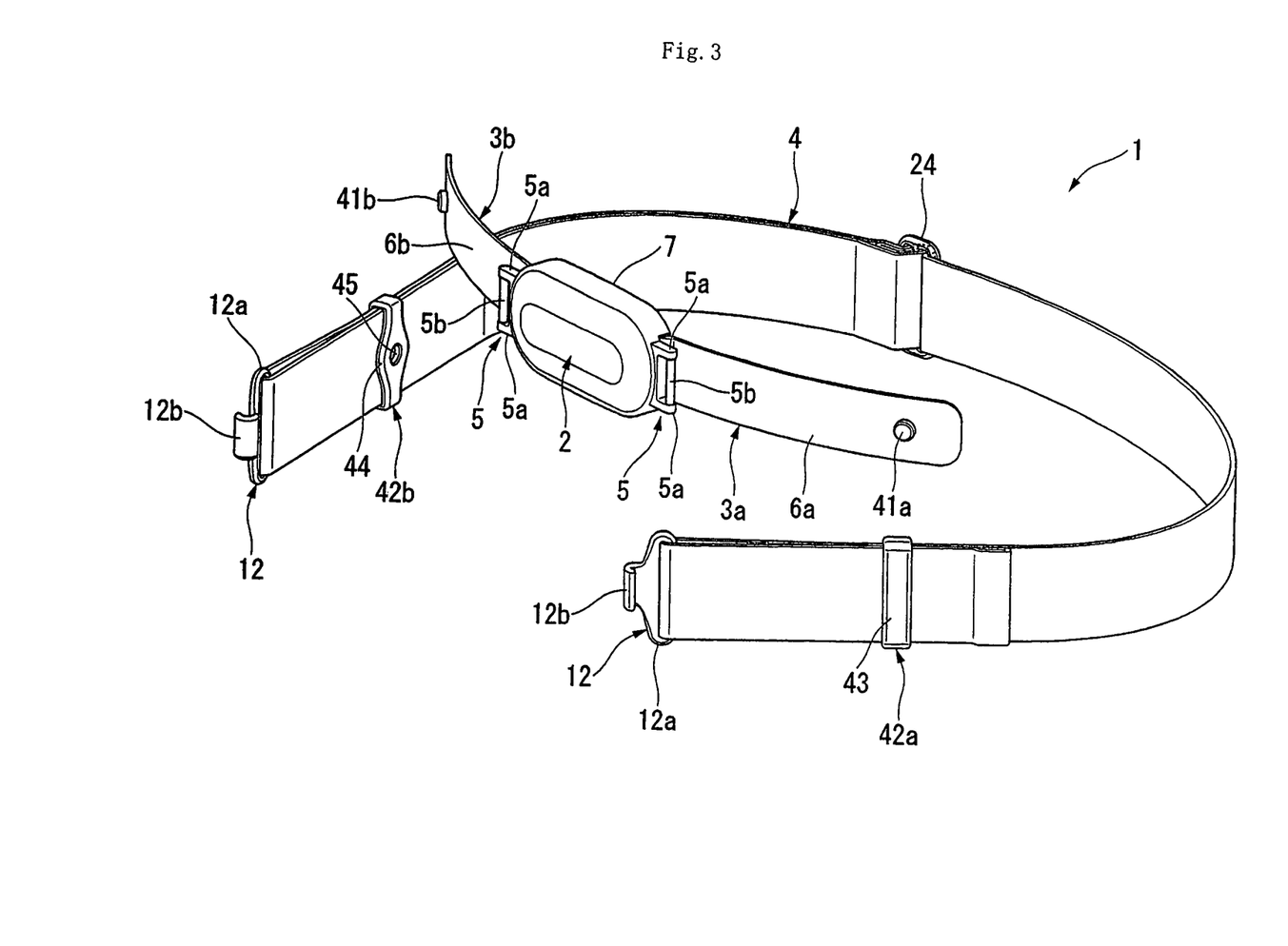
FIG. 3 is a perspective view of the heart rate measuring apparatus according to the first embodiment of the present invention.

FIG. 1 is a front view of a heart rate measuring apparatus, which is a biological information detecting apparatus according to an embodiment of the present invention, attached to a wearer. FIG. 2 is a side sectional view of the heart rate measuring apparatus attached to the wearer. FIG. 3 is a perspective view of the heart rate measuring apparatus.

As illustrated in FIGS. 1 to 3, the heart rate measuring apparatus 1 is attached to a chest that is a biological surface of the wearer S to detect cardiac signals generated in connection with heartbeats, and to communicate the detected cardiac signals via radio. As illustrated in FIG. 2, the heart rate measuring apparatus 1 includes an apparatus main body 2, a pair of heart rate detecting parts 3a, 3b that is integrally provided on both sides of the apparatus main body 2, and a fixing band (fixing part) 4 for attaching the apparatus main body 2 and the pair of heart rate detecting parts 3a, 3b to the chest of the wearer S.

The apparatus main body 2 includes a case 7 having a substantially elliptical shape in planar view, and a detection circuit board (not illustrated) provided in the case 7. Note that the external shape of the case 7 is not limited to the substantially elliptical shape as described in this embodiment, and for example, may be a rectangle.

The detection circuit board that is not illustrated includes a radio transmission unit and a transmission circuit (both not illustrated) to communicate via radio based on signals detected by the pair of heart rate detecting parts 3a, 3b. The pair of heart rate detecting parts 3a, 3b is connected electrically to the detection circuit board.

The heart rate detecting parts 3a, 3b respectively include electrodes 6a, 6b made of conductive elastomer strips. The heart rate detecting parts 3a, 3b are positioned on the both sides across the apparatus main body 2. Connecting parts 40a, 40b that are formed on one ends of the heart rate detecting parts 3a, 3b in the longitudinal direction are attached in the case 7. The connecting parts 40a, 40b are connected to the detection circuit board, so that signals detected by the electrodes 6a, 6b are output to the detection circuit board.

On the other ends of the electrodes 6a, 6b in the longitudinal direction, protrusions 41a, 41b are formed substantially at the center in the width direction. The protrusions 41a, 41b are formed in order to join the electrodes 6a, 6b and free rings 42a, 42b to be described below.

As the conductive elastomer, for example, conductive silicon rubber containing carbon black, conductive rubber containing carbon black, conductive polyurethane rubber containing carbon black, and the like can be used.

A pair of coupling members 5 is formed integrally with the case 7 at positions corresponding to the pair of electrodes 6a, 6b. Each of the coupling members 5 includes a pair of arm parts 5a and a rod-shaped engaged part 5b. The arm parts 5a extend along the strip-shaped electrodes 6a, 6b from the outer periphery of the case 7 toward the outer sides of the case 7 in radial directions, and the engaged parts 5b each extend between the pair of arm parts 5a. The engaged parts 5b of the coupling members 5 are configured to be attached to and detached from hook parts 12b of strap attaching/detaching tools 12 provided on the fixing band 4.

The fixing band 4 is a strip-shaped stretchable strap, and is substantially annular so as to be attached around the whole circumference of the chest of the wearer S. The apparatus main body 2 is coupled across the both ends of the fixing band 4 in the longitudinal direction.

A length adjuster 24 for adjusting the length of the fixing band 4 is provided substantially at the center of the fixing band 4 in the longitudinal direction.

On the both ends of the fixing band 4 in the longitudinal direction, the strap attaching/detaching tools 12 for detachably attaching the fixing band 4 to the apparatus main body 2 are provided. Each of the strap attaching/detaching tools 12 includes a substantially elliptical annular frame 12a and a hook part 12b that is formed to curve from an area along the longitudinal direction of the frame 12a toward the outer side in the radial direction of the frame 12a. The frame 12a and the hook part 12b may be integrally formed, or may be formed separately and then joined.

The strap attaching/detaching tools 12 configured as described above are attached to the fixing band 4 in a manner described below. Each end of the fixing band 4 is inserted through the frame 12a of the strap attaching/detaching tool 12, and the end is thereafter folded back to the side opposite to the hook part 12b and then adhered to the fixing band 4 itself. In this manner, the strap attaching/detaching tools 12 are attached to the both ends of the fixing band 4 in the longitudinal direction.

The hook parts 12b of the strap attaching/detaching tools 12 are then engaged with the engaged parts 5b of the coupling members 5 that are integrally formed with the apparatus main body 2, whereby the fixing band 4 is attached to the apparatus main body 2. With the fixing band 4 attached to the apparatus main body 2, the heart rate detecting parts 3a, 3b are positioned between the fixing band 4 and the chest of the wearer S. This means that, when the heart rate measuring apparatus 1 is attached to the wearer S, the fixing band 4 covers the heart rate detecting parts 3a, 3b and has functions of pressing the heart rate detecting parts 3a, 3b to the chest of the wearer S and of maintaining the connection between the chest and the heart rate detecting parts 3a, 3b.

On the both ends of the fixing band 4, the free rings 42a, 42b are respectively attached.

Figure 4:
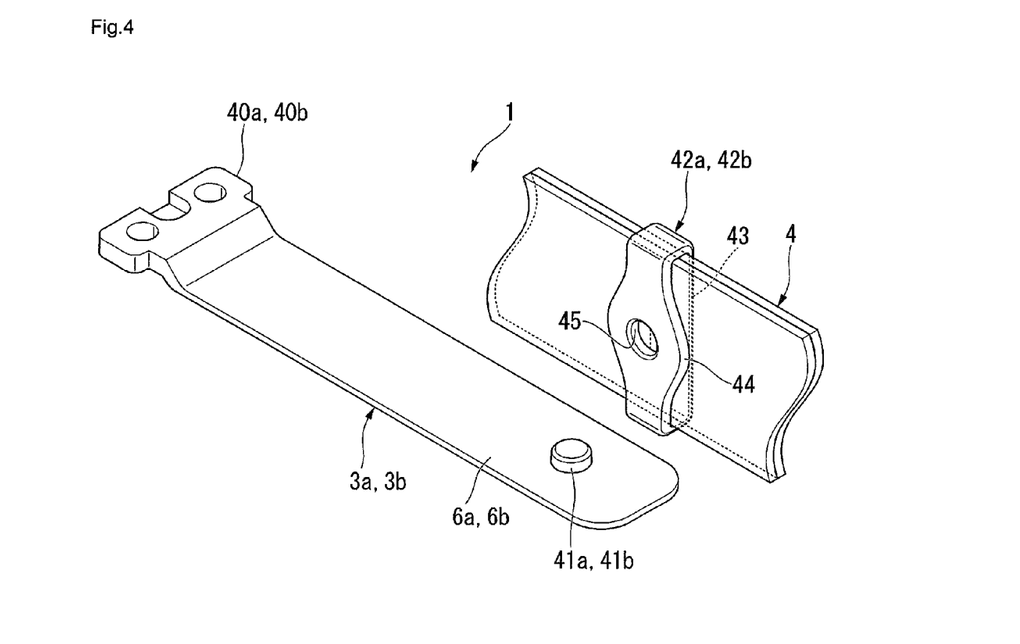
FIG. 4 is an enlarged perspective view of a free ring and a heart rate detecting part according to the first embodiment of the present invention.

FIG. 4 is an enlarged perspective view of the free ring and the heart rate detecting part.

As illustrated in FIGS. 3 and 4, the free rings 42a, 42b are formed to surround the circumference of the fixing band 4 in the short-length direction. Each of the free rings 42a, 42b includes a substantially elliptical annular free ring body (holder) 43 and a joining part 44 integrally formed with the free ring body 43 on the side of each of the heart rate detecting parts 3a, 3b of the free ring body 43.

The joining part 44 is formed to be gradually wider toward the center of the fixing band 4 in the short-length direction. In the center portions of the joining parts 44, there are formed recesses 45 into which the protrusions 41a, 41b formed on the heart rate detecting parts 3a, 3b are press-fitted. Instead of the recesses 45, holes into which the protrusions 41a, 41b can be press-fitted may be formed in the joining parts 44.

With this configuration, the press-fit of the protrusions 41a, 41b of the heart rate detecting parts 3a, 3b into the recesses 45 of the joining parts 44 joins the free rings 42a, 42b and the heart rate detecting parts 3a, 3b. When the heart rate measuring apparatus 1 in this state is attached to the chest of the wearer S, portions of the fixing band 4 where the free rings 42a, 42b are attached stick out from the level of the other portions, whereby portions corresponding to the free rings 42a, 42b of the electrodes 6a, 6b are strongly pressed to the chest of the wearer S.

That is, portions corresponding to the protrusions 41a, 41b formed on the sides of the electrodes 6a, 6b opposite to the chest are strongly pressed to the chest. In other words, portions of the electrodes 6a, 6b at positions corresponding to right and left outer positions of the chest of the wearer S are strongly pressed.

Then, cardiac signals generated in connection with heartbeats are detect by the pair of the electrodes 6a, 6b. The detection circuit board (not illustrated) of the apparatus main body 2 communicates the cardiac signals detected by the pair of the electrodes 6a, 6b via radio.

In this embodiment, since the free rings 42a, 42b are attached to the fixing band 4, the electrodes 6a, 6b joined to these free rings 42a, 42b do not deviate with respect to the fixing band 4. In addition, since the free rings 42a, 42b are attached slidably in the longitudinal direction of the fixing band 4, for example, even when the fixing band 4 expands or contracts according to movement of the wearer S, the free rings 42a, 42b slide on the fixing band 4. Thus, the positions of the free rings 42a, 42b themselves with respect to the wearer S do not change.

Therefore, according to the above first embodiment, contact states and contact positions of the electrodes 6a, 6b with respect to the chest of the wearer S can be prevented from being unstable. Thus, cardiac signals can be detected favorably by the electrodes 6a, 6b.

In addition, since the free rings 42a, 42b strongly press the portions of the electrodes 6a, 6b at the positions corresponding to the right and left outer positions of the chest concentrically, detection accuracy of cardiac signals can be improved.

In order to join the heart rate detecting parts 3a, 3b and the free rings 42a, 42b, the protrusions 41a, 41b are formed at the other ends of the electrodes 6a, 6b of the heart rate detecting parts 3a, 3b in the longitudinal direction. Meanwhile, the joining parts 44 are formed on the free rings 42a, 42b attached to the fixing band 4. In the joining parts 44, the recesses 45 into which the protrusions 41a, 41b are press-fitted are formed. As described above, since the heart rate detecting parts 3a, 3b and the free rings 42a, 42b are joined with a simple structure, it is possible to suppress an increase in size of the entire heart rate measuring apparatus 1, and an increase in manufacturing costs. In addition, since the heart rate detecting parts 3a, 3b and the free rings 42a, 42b are joined reliably, connection between the chest of the wearer S and the electrodes 6a, 6b can be maintained reliably.

Second Embodiment

Next, a second embodiment of the present invention will be described with reference to FIG. 5. Note that, similar reference signs are used for components that are similar to those in the first embodiment (the same applies to embodiments to be described below).

Figure 5:
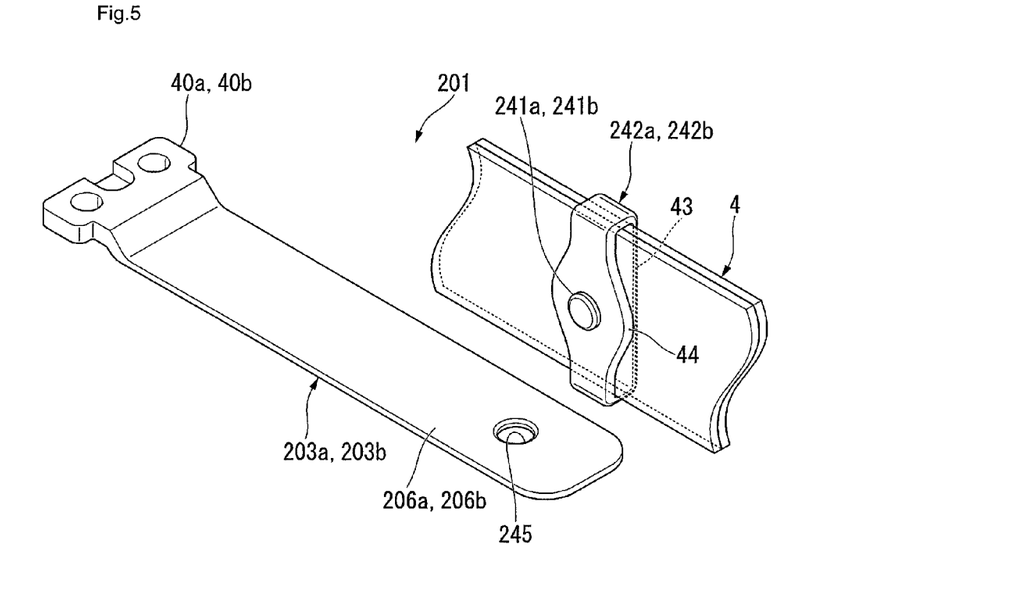
FIG. 5 is an enlarged perspective view of a free ring and a heart rate detecting part according to a second embodiment of the present invention.

FIG. 5 is an enlarged perspective view of a free ring and a heart rate detecting part of this second embodiment and corresponds to FIG. 4 of the above first embodiment (the same applies to embodiments to be described below).

A basic configuration in the second embodiment is similar to that in the above first embodiment (the same applies to embodiments to be described below) in the following points, for example. That is, a heart rate measuring apparatus 201 includes the apparatus main body 2, a pair of heart rate detecting parts 203a, 203b that is integrally provided on both sides of the apparatus main body 2, and the fixing band 4 for attaching the apparatus main body 2 and the pair of the heart rate detecting parts 203a, 203b to the chest of the wearer S. The respective heart rate detecting parts 203a, 203b are positioned on the both sides across the apparatus main body 2, and the connecting parts 40a, 40b formed on one ends of the heart rate detecting parts 203a, 203b in the longitudinal direction are attached in the case 7. Furthermore, free rings 242a, 242b are provided on the fixing band 4 slidably along the longitudinal direction of the fixing band 4.

As illustrated in FIG. 5, the difference between the second embodiment and the above first embodiment is as follows. In the first embodiment, the protrusions 41a, 41b are respectively formed at the other ends of the electrodes 6a, 6b in the longitudinal direction and the recesses 45, into which the protrusions 41a, 41b are press-fitted, are formed on the free rings 42a, 42b. In the second embodiment, on the other hand, protrusions 241a, 241b are formed on the free rings 242a, 242b and recesses 245, into which the protrusions 241a, 241b are respectively press-fitted, are formed on the other ends of electrodes 206a, 206b in the longitudinal direction.

As described above, the protrusions 241a, 241b and the recesses 245 formed inversely to the above first embodiment can achieve an effect similar to the first embodiment.

Third Embodiment

Next, a third embodiment of the present invention will be described with reference to FIG. 6.

Figure 6:
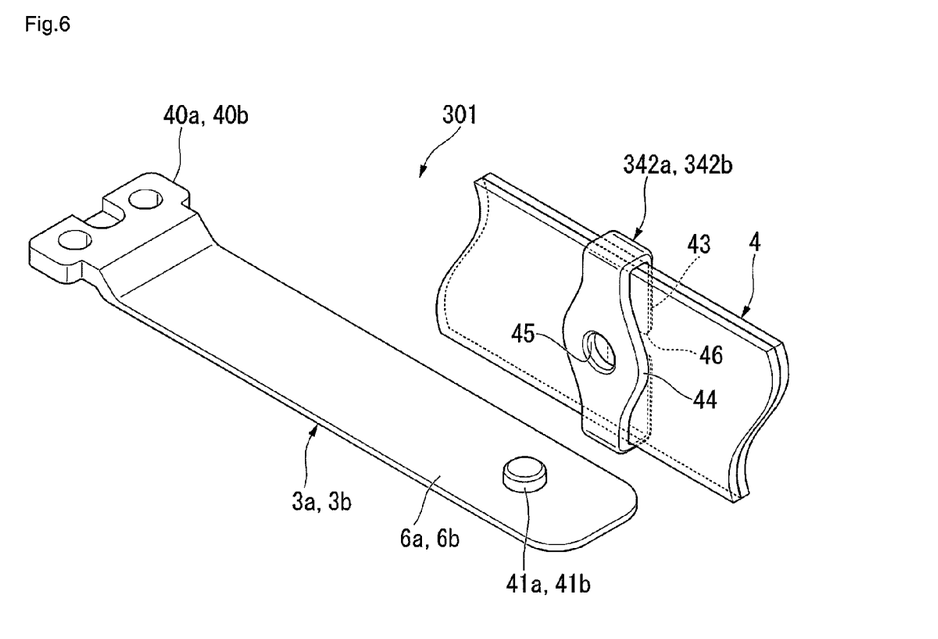
FIG. 6 is an enlarged perspective view of a free ring and a heart rate detecting part according to a third embodiment of the present invention.

FIG. 6 is an enlarged perspective view of a free ring and a heart rate detecting part of this third embodiment.

As illustrated in FIG. 6, the difference between the third embodiment and the above first embodiment is that a slit 46 is formed substantially in the center of each of free rings 342a, 342b of a heart rate measuring apparatus 301 of the third embodiment so as to cut the free ring body 43 in the short-length direction while the slit 46 is not formed in the free rings 42a, 42b of the above first embodiment.

With this configuration, when the free rings 342a, 342b are attached to the fixing band 4, the fixing band 4 is inserted through the slit 46. That is, after the heart rate measuring apparatus 301 is assembled, only the free rings 342a, 342b can be attached to and detached from the fixing band 4.

Therefore, the above third embodiment can improve workability upon maintenance such as cleaning of the fixing band 4 in addition to an effect similar to the above first embodiment.

Fourth Embodiment

Next, a fourth embodiment of the present invention will be described with reference to FIG. 7.

Figure 7:
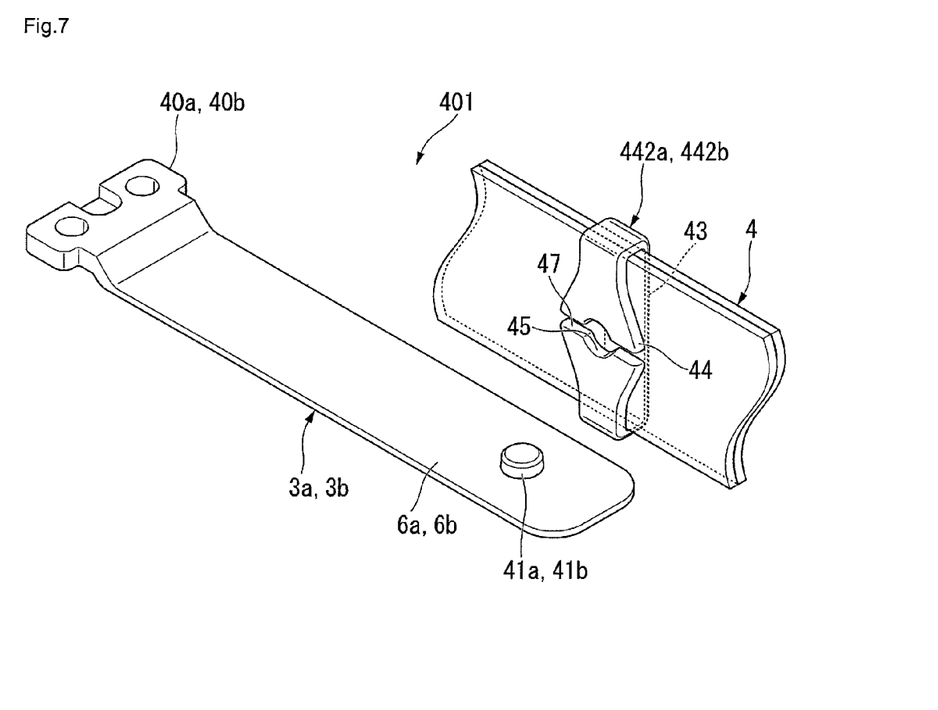
FIG. 7 is an enlarged perspective view of a free ring and a heart rate detecting part according to a fourth embodiment of the present invention.

FIG. 7 is an enlarged perspective view of a free ring and a heart rate detecting part of this fourth embodiment.

As illustrated in FIG. 7, the difference between the fourth embodiment and the above third embodiment is that the slit 46 is formed in each of the free rings 342a, 342b of the third embodiment so as to cut the free ring body 43 while a slit 47 is formed in each of free rings 442a, 442b of a heart rate measuring apparatus 401 of the fourth embodiment so as to cut a portion on the side of the joining part 44 where the recess 45 is formed.

With this configuration, when the protrusions 41a, 41b on the heart rate detecting parts 3a, 3b are press-fitted into the recesses 45 on the free ring 442a, 442b, the recesses 45 are slightly pushed apart. That is, a press-fit force can be maintained almost constant without controlling a press-fit allowance of the protrusions 41a, 41b against the recesses 45 with high accuracy. Therefore, manufacturing accuracy requirements of the recesses 45 and the protrusions 41, 41b can be reduced, making it possible to reduce manufacturing cost.

Fifth Embodiment

Next, a fifth embodiment of the present invention will be described with reference to FIG. 8.

Figure 8:
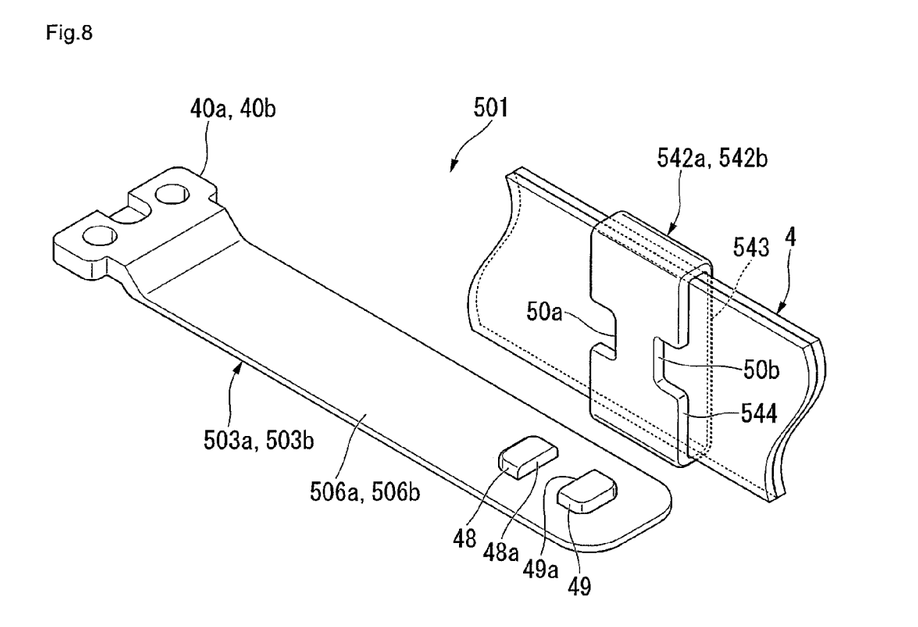
FIG. 8 is an enlarged perspective view of a free ring and a heart rate detecting part according to a fifth embodiment of the present invention.

FIG. 8 is an enlarged perspective view of a free ring and a heart rate detecting part of this fifth embodiment.

As illustrated in FIG. 8, the difference between the fifth embodiment and the above first embodiment is that the shape of the protrusions 41a, 41b formed on the electrodes 6a, 6b and the shape of the free rings 42a, 42b of the above first embodiment are different from shapes of protrusions 48, 49 formed on electrodes 506a, 506b of a heart rate measuring apparatus 501 of the fifth embodiment and a shape of free rings 542a, 542b.

More specifically, on the electrodes 506a, 506b of the heart rate detecting parts 503a, 503b, the pair of protrusions 48, 49 is formed instead of the protrusions 41a, 41b of the above first embodiment. These protrusions 48, 49 are arranged side by side along the longitudinal direction of each of the heart rate detecting parts 503a, 503b. Surfaces 48a, 49a of the respective protrusions 48, 49 that face each other are formed to be flat.

Meanwhile, each of the free rings 542a, 542b includes a free ring body 543 formed to surround the circumference of the fixing band 4 in the short-length direction and a joining part 544 integrally formed on each of the heart rate detecting parts 503a, 503b sides of the free ring body 543, the free ring body 543 and the joining part 544 having an identical width. On both sides of the joining part 544 in the short-length direction, recesses 50a, 50b capable of receiving the protrusions 48, 49 are formed at portions corresponding to these protrusions 48, 49.

A distance L1 between the protrusions 48, 49 of each of the electrodes 506a, 506b and a width W1 between the recesses 50a, 50b formed in the joining part 544 of each of the free rings 542a, 542b are set to be substantially identical. Alternatively, the width W1 is set to be slightly larger than the distance L1.

With this configuration, the electrodes 506a, 506b and the free rings 542a, 542b can be joined by fitting the joining parts 544 of the free rings 542a, 542b between the protrusions 48, 49 of the electrodes 506a, 506b. In addition, since the recesses 50a, 50b are formed in the joining part 544 of each of the free rings 542a, 542b and the protrusions 48, 49 are inserted into the recesses 50a, 50b, it is possible to regulate deviation of the electrodes 506a, 506b in the width direction with respect to the fixing band 4.

Therefore, the above fifth embodiment can achieve an effect similar to the above first embodiment.

Sixth Embodiment

Next, a sixth embodiment of the present invention will be described with reference to FIG. 9.

Figure 9:
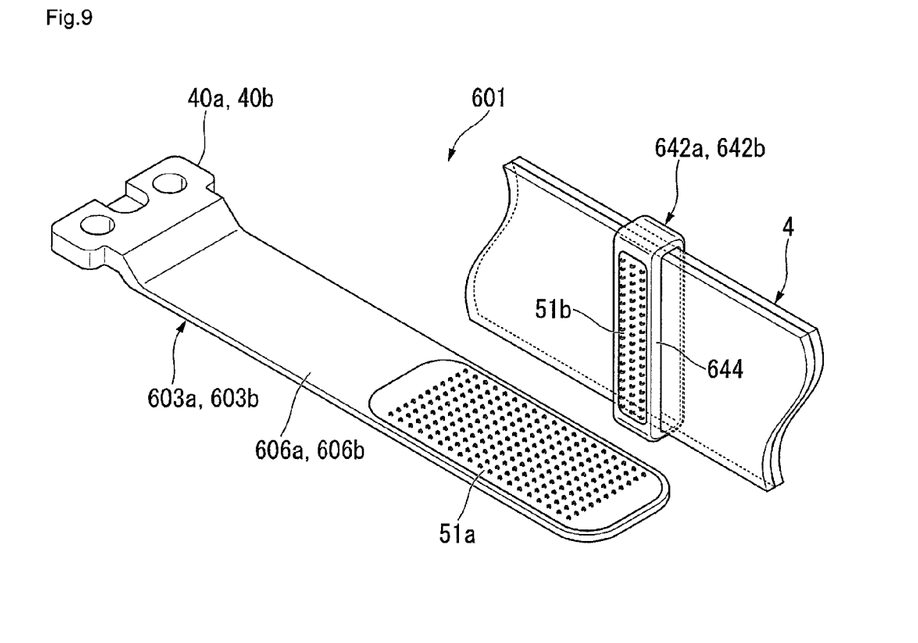
FIG. 9 is an enlarged perspective view of a free ring and a heart rate detecting part according to a sixth embodiment of the present invention.

FIG. 9 is an enlarged perspective view of a free ring and a heart rate detecting part of this sixth embodiment.

As illustrated in FIG. 9, the difference between the sixth embodiment and the above fifth embodiment is that in each of heart rate detecting parts 603a, 603b of a heart rate measuring apparatus 601 of the sixth embodiment, a first surface fastener 51a is provided on each of electrodes 606a, 606b instead of the protrusions 48, 49 while a second surface fastener 51b that can be engaged with and disengaged from the first surface fastener 51a is formed on a joining part 644 of each of free rings 642a, 642b.

The first surface fastener 51a is formed to have a substantially rectangular shape in planar view along the longitudinal direction of the electrodes 606a, 606b. Meanwhile, the second surface fastener 51b is formed to have a substantially rectangular shape in planar view along the circumferential direction of the free rings 642a, 642b. That is, the free rings 642a, 642b can be attached to any portions of the heart rate detecting parts 603a, 603b where the first surface fasteners 51a are formed.

Therefore, according to the above sixth embodiment, positions for attaching the free rings 642a, 642b to the heart rate detecting parts 603a, 603b can be adjusted, and thus positions of the electrodes 606a, 606b that are optimum for each wearer S can be pressed, which results in stable and favorable biological signal detection in addition to an effect similar to the above first embodiment.

Seventh Embodiment

Next, a seventh embodiment of the present invention will be described with reference to FIG. 10.

Figure 10:
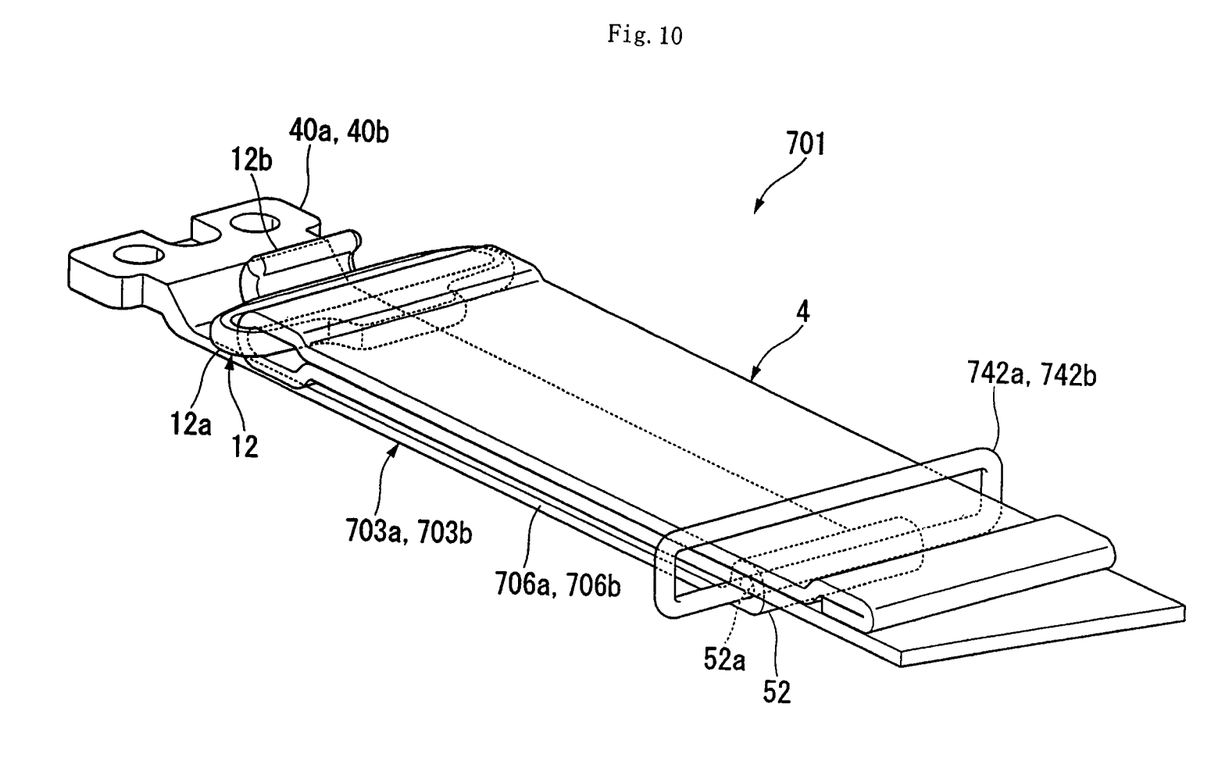
FIG. 10 is an enlarged perspective view of a free ring and a heart rate detecting part according to a seventh embodiment of the present invention.

FIG. 10 is an enlarged perspective view of a free ring and a heart rate detecting part of this seventh embodiment.

As illustrated in FIG. 10, the difference between the seventh embodiment and the above first embodiment is that in a heart rate measuring apparatus 701 of the seventh embodiment, rings 742a, 742b and heart rate detecting parts 703a, 703b are integrated while the corresponding parts are not integrated in the first embodiment.

More specifically, on the other ends of electrodes 706a, 706b of the heart rate detecting parts 703a, 703b in the longitudinal direction, that is, on the ends opposite to the connecting parts 40a, 40b, cylindrical parts 52 are formed over the electrodes 706a, 706b in the short-length direction. A hole 52a of each of the cylindrical parts 52 is formed along the short-length direction of the electrodes 706a, 706b.

Meanwhile, the rings 742a, 742b are provided to surround the circumference of the fixing band 4 in the short-length direction, and these rings 742a, 742b are inserted through the holes 52a of the cylindrical parts 52 formed over the electrodes 706a, 706b so as to be attached. That is, the cylindrical parts 52 serve as joining parts that join the heart rate detecting parts 703a, 703b and the rings 742a, 742b.

Note that, in this seventh embodiment, similarly to the above embodiments, the apparatus main body 2 and the fixing band 4 can be detachable. Specifically, for example, the wearer S releases the engagement between the engaged parts 5b and the hook parts 12b of the strap attaching/detaching tools 12 (unhooks the hook parts 12b from the engaged parts 5b), and inserts the hook parts 12b through the holes of the rings 742a, 742b.

Therefore, according to the above seventh embodiment, the rings 742a, 742b and the electrodes 706a, 706b are integrated through the cylindrical parts 52. Thus, part management can be easy, and assemblability of the heart rate measuring apparatus 701 can be improved.

Note that the rings 742a, 742b having a substantially C-shape, for example, can be employed and both (free) ends thereof are inserted into the holes 52a. Alternatively, the rings 742a, 742b having a substantially O-shape can be employed and the rings 742a, 742b are integrally formed with the electrodes 706a, 706b.

Note that the present invention is not limited to the above embodiments, and includes various modifications of the above embodiments without departing from the spirit of the present invention.

For example, in the above embodiments, there has been described a case where the apparatus main bodies 2 and the heart rate detecting parts 3a to 703b are integrally formed, and these apparatus main bodies 2 and the heart rate detecting parts 3a to 703b are attached to the chest of the wearer S using the fixing band 4 in the heart rate measuring apparatuses 1 to 701 that measure heart rate of the wearer S as a biological information detecting apparatus. However, the configuration is not limited thereto, and the invention can be applied to various biological information detecting apparatuses. That is, the configurations of the above embodiments can be applied to an apparatus that measures blood pressure, body temperature, myogenic potential, or the like as a biological information detecting apparatus.

In addition, there has been described a case where the fixing band 4 is a stretchable strap formed to have a strip shape in the above embodiments. However, the fixing band 4 is not limited thereto and the fixing band 4 can be formed using a non-stretchable material.

Further, there has been described a case where one of the free rings 42a to 742b is attached on each of the both sides of the fixing band 4 in the above embodiments. However, the number of the free rings 42a to 742b attached to the fixing band 4 is not limited to two, and three or more of the free rings 42a to 742b can be provided.

What is claimed is:

1. A biological information detecting apparatus comprising:
   an apparatus main body;
   a pair of biological signal detecting parts provided on the apparatus main body, each of the biological signal detecting parts having an electrode adapted to be in contact with a biological surface of a user's body;
   a strip-shaped fixing part attached to the apparatus main body and configured to fix the apparatus main body and the pair of biological signal detecting parts to the user's body;
   holders provided to be slidable along a longitudinal direction of the fixing part; and
   joining parts configured to releasably join the pair of biological signal detecting parts to the respective holders.

2. The biological information detecting apparatus according to claim 1, wherein the holders are positioned at portions corresponding to ends, which are opposite to the apparatus main body, of the electrodes.

3. The biological information detecting apparatus according to claim 1, wherein each of the joining parts includes a protrusion provided on the biological signal detecting part and a recess provided on the holder and capable of receiving the protrusion.

4. The biological information detecting apparatus according to claim 3, wherein the protrusion is press-fitted into the recess.

5. The biological information detecting apparatus according to claim 3, wherein each of the holders is formed to surround a circumference of the fixing part in a short-length direction thereof, and a slit is formed to cut the holder in a short-length direction thereof.

6. The biological information detecting apparatus according to claim 5, wherein the slit is formed to cut a portion of the holder where the recess is formed.

7. The biological information detecting apparatus according to claim 1, wherein each of the joining parts includes surface fasteners respectively provided on each of the biological signal detecting parts and each of the holders.

8. The biological information detecting apparatus according to claim 1, wherein each of the joining parts includes a protrusion provided on the holder and a recess provided on the biological signal detecting part for receiving the protrusion.

9. The biological information detecting apparatus according to claim 8, wherein the protrusion is configured to be press-fitted into the recess.

10. The biological information detecting apparatus according to claim 1, wherein each of the holders is configured so as to completely surround the fixing part.

11. The biological information detecting apparatus according to claim 1, wherein the joining parts comprise a pair of protrusions provide on each of the biological signal detecting parts and a pair of recesses formed on each of the holders for receiving the pair of protrusions.

12. The biological information detecting apparatus according to claim 1, wherein each of the holders is configured to be slidable along the longitudinal direction of the fixing part when the signal detecting part is not joined to the holder by the joining parts.

13. The biological information detecting apparatus according to claim 1, wherein each of the holders is configured to at least partially surround the fixing part when the signal detecting part is not joined to the holder by the joining parts.

14. A biological information detecting apparatus comprising:
an apparatus main body;
a pair of biological signal detecting parts provided on the apparatus main body, each of the biological signal detecting parts having an electrode adapted to be in contact with a biological surface of a user's body;
a strip-shaped fixing part attached to the apparatus main body and configured to fix the apparatus main body and the pair of biological signal detecting parts to the user's body;
holders provided to be slidable along a longitudinal direction of the fixing part; and
joining parts configured to join the pair of biological signal detecting parts to the respective holders;
wherein each of the biological signal detecting parts, each of the holders, and each of the joining parts are formed integrally with one another, each of the joining parts having a hole and being formed integrally with the corresponding detecting part, and each of the holders having a portion inserted into the hole of the corresponding joining part so as to be connected integrally with the corresponding joining part.

15. A fixing structure comprising:
a pair of biological signal detecting parts provided on an apparatus main body, each of the biological signal detecting parts having an electrode adapted to be in contact with a biological surface of a user's body;
a strip-shaped fixing part attached to the apparatus main body and configured to fix the apparatus main body and the pair of biological signal detecting parts to the user's body;
holders provided to be slidable along a longitudinal direction of the fixing part; and
joining parts configured to releasably join the pair of biological signal detecting parts to the respective holders;
wherein the fixing part, the holders, and the joining parts are configured to fix the biological signal detecting parts to the user's body.

16. The fixing structure according to claim 15, wherein each of the joining parts includes a protrusion provided on one of the biological signal detecting part and the holder and a recess provided on the other of the biological detecting part and the holder for receiving the protrusion.

17. The fixing structure according to claim 15, wherein each of the joining parts includes surface fasteners respectively provided on each of the biological signal detecting parts and each of the holders.

18. A biological information detecting apparatus comprising:
an apparatus main body;
a pair of biological signal detecting parts provided on the apparatus main body, each of the biological signal detecting parts having an electrode adapted to be in contact with a biological surface of a user's body;
a fixing part configured for removable attachment to the apparatus main body for fixedly mounting the apparatus main body and the pair of biological signal detecting parts to the user's body; and
holders configured to be releasably joined to the respective electrodes of the biological signal detecting parts while being slidably mounted to the fixing part so that the holders concentrically press the electrodes against the biological surface of the user's body and undergo sliding movement relative to the fixing part as a result of expansion and contraction of the fixing part due to movement of the user's body.

19. The biological information detecting apparatus according to claim 18, further comprising joining parts for releasably joining the holders to the respective electrodes of the biological signal detecting parts, the joining parts comprising a protrusion provided on one of the biological signal detecting part and the holder and a recess provided on the other of the biological detecting part and the holder for receiving the protrusion.

20. The biological information detecting apparatus according to claim 18, further comprising joining parts for releasably joining the holders to the respective electrodes of the biological signal detecting parts, the joining parts comprising surface fasteners respectively provided on each of electrodes and each of the holders.

* * * * *